(12) United States Patent  
Smith

(10) Patent No.: US 8,931,489 B2  
(45) Date of Patent: Jan. 13, 2015

(54) HEARING PROTECTION DEVICES AND KITS INCLUDING ADJUSTABLE SOUND-ATTENUATION ASSEMBLIES

(71) Applicant: So Others May Hear, LLC, Dayton, OH (US)

(72) Inventor: Jeremiah Smith, Dayton, OH (US)

(73) Assignee: So Others May Hear, LLC, Dayton, OH (US)

( * ) Notice: Subject to any disclaimer, the term of this patent is extended or adjusted under 35 U.S.C. 154(b) by 173 days.

(21) Appl. No.: 13/735,177

(22) Filed: Jan. 7, 2013

(65) Prior Publication Data

US 2014/0190493 A1 Jul. 10, 2014

(51) Int. Cl.
*A61F 11/08* (2006.01)

(52) U.S. Cl.
CPC ........... *A61F 11/08* (2013.01); *A61F 2011/085* (2013.01)
USPC .......................................... 128/867; 128/864

(58) Field of Classification Search
USPC ......... 181/129–130, 134–135, 294; D24/106, D24/112, 174; 2/68, 209, 918; 381/324, 381/123, 72; 128/846–867
See application file for complete search history.

(56) References Cited

U.S. PATENT DOCUMENTS

| | | | |
|---|---|---|---|
| 2,521,414 A | 9/1950 | Schier | |
| 4,540,063 A | 9/1985 | Ochi et al. | |
| 5,332,871 A | 7/1994 | Carrigan | |
| 6,082,485 A * | 7/2000 | Smith | 181/135 |
| 6,148,821 A | 11/2000 | Falco | |
| 6,286,622 B1 | 9/2001 | Tiemann | |
| 7,182,087 B1 | 2/2007 | Marsh | |
| 7,512,243 B2 | 3/2009 | Haussmann | |
| 7,793,662 B2 | 9/2010 | Elliott | |
| 7,889,883 B2 * | 2/2011 | Cartwright et al. | 381/380 |
| 8,113,207 B2 | 2/2012 | Gehling et al. | |
| 2007/0102006 A1 * | 5/2007 | Falco | 128/864 |

FOREIGN PATENT DOCUMENTS

EP 0 333 298 B1 6/1993
EP 1 795 160 B1 5/2009

* cited by examiner

*Primary Examiner* — Alireza Nia
*Assistant Examiner* — Ophelia A Hawthorne
(74) *Attorney, Agent, or Firm* — Dinsmore & Shohl, LLP

(57) ABSTRACT

Hearing protection devices and kits may include an earplug body and an adjustable sound attenuation assembly composed of an attenuator case and an attenuator insert that is removably insertable into the attenuator case. The attenuator case has a hollow barrel portion that accommodates the attenuator insert and a hollow extension portion connected to the hollow barrel portion. The hollow extension portion includes a soundpath channel therethrough defining a soundpath axis. The attenuator insert is rotatable within the hollow barrel portion of the attenuator case about a rotation axis that is noncollinear with the soundpath axis. The attenuator insert has a thickness along the soundpath axis that varies with respect to a rotation angle of the attenuator insert within the attenuator case. Thereby, sound waves that enter the soundpath channel through the distal opening are attenuated proportionally to the thickness of the attenuator insert along the soundpath axis.

17 Claims, 11 Drawing Sheets

HEARING PROTECTION DEVICES AND KITS INCLUDING ADJUSTABLE SOUND-ATTENUATION ASSEMBLIES

TECHNICAL FIELD

The present disclosure relates to hearing protection devices and, more particularly, to hearing protection devices and kits that facilitate adjustable sound attenuation.

BACKGROUND

Prolonged or repeated exposure to loud noises or high volume of sound is the leading cause of hearing loss. Common devices such as earplugs that can be inserted into the ear canal or ear muffs that are worn over the ears may be effective at lowering exposures to loud noises. Nevertheless, such devices must be removed to enable the user to hear voices in their environment after loud noises cease, thereby causing inconvenience or risk that the device will be inaccessible when the loud noises resume. There remain ongoing needs for simple hearing protection devices that are both convenient and effective at lowering the volume of ambient sounds to safe levels.

SUMMARY

Against the above background, some embodiments described herein are directed to hearing protection devices that may include an earplug body and an adjustable sound attenuation assembly. The earplug body may include a canal portion that is insertable into an ear canal of an ear; a canal opening at a proximal end of the canal portion that opens into the ear canal when the canal portion is inserted into the ear canal; and an outer portion that is disposed in the concha bowl of the ear when the canal portion is inserted into the ear canal. The adjustable sound attenuation assembly may include an attenuator case disposed in the earplug body and an attenuator insert that is removably insertable into the attenuator case. The attenuator case may include a hollow barrel portion that accommodates the attenuator insert therein; and a hollow extension portion connected to the hollow barrel portion, the hollow extension portion of the attenuator case being disposed in the canal portion of the earplug body. The hollow extension portion includes a soundpath channel defined therethrough, the soundpath channel having a distal opening into the hollow barrel portion and a proximal opening opposite the distal opening. The soundpath channel may define a soundpath axis. The attenuator insert may be rotatable within the hollow barrel portion of the attenuator case about an insert rotation axis that may be noncollinear with the soundpath axis. The attenuator insert has a thickness along the soundpath axis that varies with respect to a rotation angle of the attenuator insert within the attenuator case. Thereby, sound waves that enter the soundpath channel through the distal opening are attenuated proportionally to the thickness of the attenuator insert along the soundpath axis.

Further embodiments described herein are directed to hearing protection kits that may include at least one earplug body having an attenuator case therein and may also include at least one attenuator insert. Each earplug body in the hearing protection kits may include a canal portion that is insertable into an ear canal of an ear; a canal opening at a proximal end of the canal portion that opens into the ear canal when the canal portion is inserted into the ear canal; and an outer portion that is disposed in the concha bowl of the ear when the canal portion is inserted into the ear canal. The attenuator case disposed in the earplug body may include a hollow barrel portion that accommodates the attenuator insert therein; and a hollow extension portion connected to the hollow barrel portion. The hollow extension portion of the attenuator case may be disposed in the canal portion of the earplug body. The hollow extension portion has a soundpath channel defined therethrough. The soundpath channel has a distal opening into the hollow barrel portion and a proximal opening opposite the distal opening. The soundpath channel may define a soundpath axis. Each attenuator insert in the hearing protection kits may rotatable within the hollow barrel portion of the attenuator case in the earplug body about an insert rotation axis. The insert rotation axis may be noncollinear with the soundpath axis. The at least one attenuator insert may have a thickness along the soundpath axis that varies with respect to a rotation angle of the at least one attenuator insert within the at least one attenuator case. The at least one attenuator insert may have a maximum thickness along the soundpath axis that defines a maximum attenuation of the at least one attenuator insert. When the kit is assembled with the at least one attenuator insert being inserted into the at least one attenuator case, sound waves that enter the soundpath channel through the distal opening may be attenuated proportionally to the thickness of the attenuator insert along the soundpath axis.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

It should be understood that the figures are provided in an enlarged scale and that components depicted in the figures may not be to scale in relation to each other.

DETAILED DESCRIPTION

Embodiments of hearing protection devices are described that may enable a user or wearer of the devices to adjust an amount of sound attenuation without removing the hearing protection device. The hearing protection devices according to preferred embodiments described herein may operate based on mechanical principles alone and may not require electronic circuitry to accomplish the sound attenuation. The hearing protection devices according to some embodiments may include positions representing minimal or zero sound attenuation and other positions representing maximum attenuation. Thereby, the devices may be worn even when external noises are minimal, such as in a conversational environment, for example, and may be subsequently switched to maximum attenuation when required, such as when the wearer walks onto an aircraft tarmac, encounters sudden gunfire, partakes in a loud sporting event, or serves as a member of a pit crew in an automobile race, for example. The hearing protection devices may also have desirable benefits on the battlefield, such as to a sniper who needs to listen clearly to orders or even to the silence of nature unattenuated and then, after realizing a need to discharge a loud firearm, must quickly switch the hearing protection device to maximum attenuation.

Embodiments of hearing protection devices will now be described first generally with reference to FIGS. 1-5 then in greater detail with reference to FIGS. 1-13B. Embodiments of kits containing the hearing protection devices will be described below, for which description FIGS. 1-13B will also be beneficial in gaining an understanding of the components of the kits.

Figure 1:
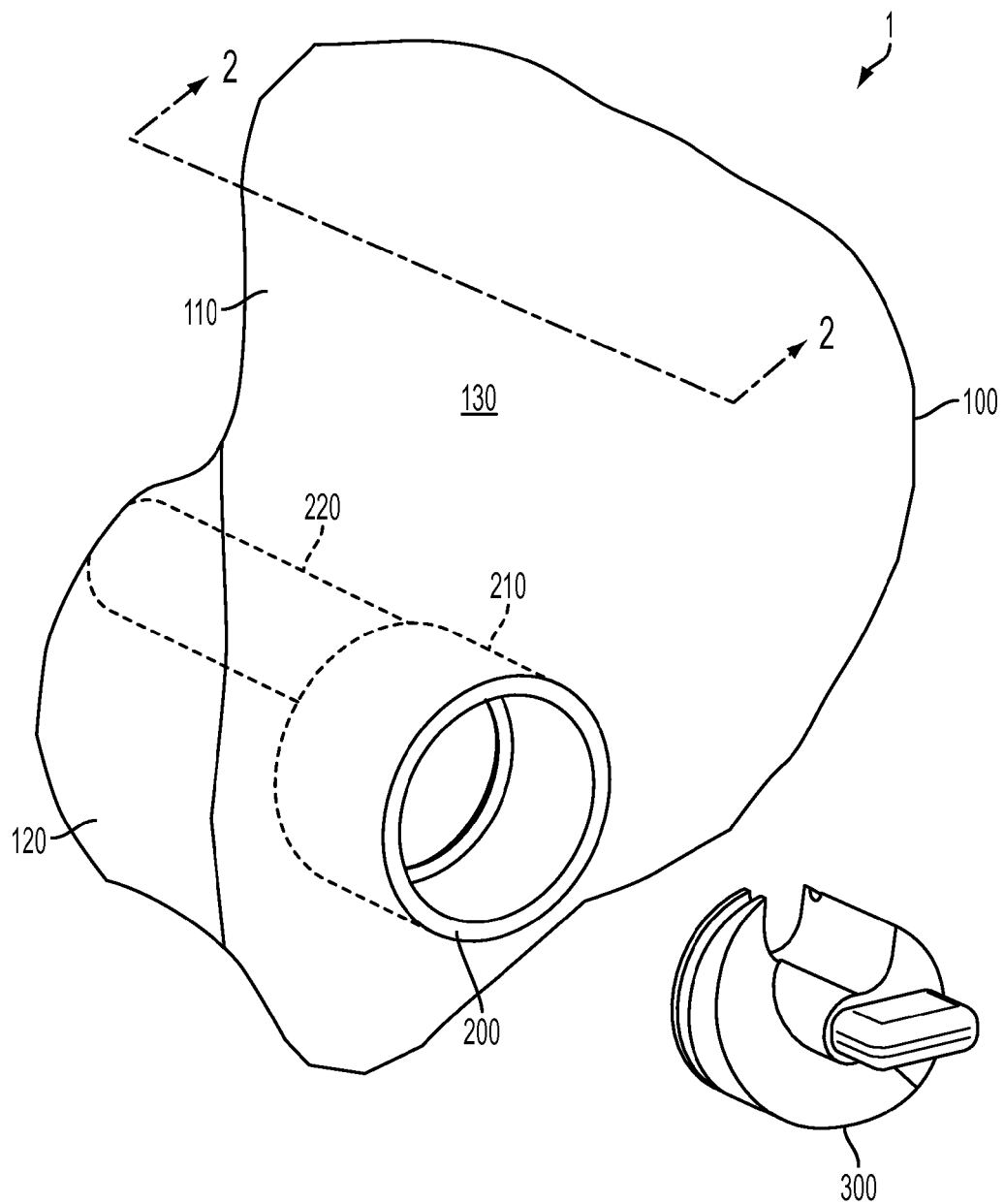
FIG. 1 is an exploded view of a hearing protection device according to embodiments described herein.
Figure 2:
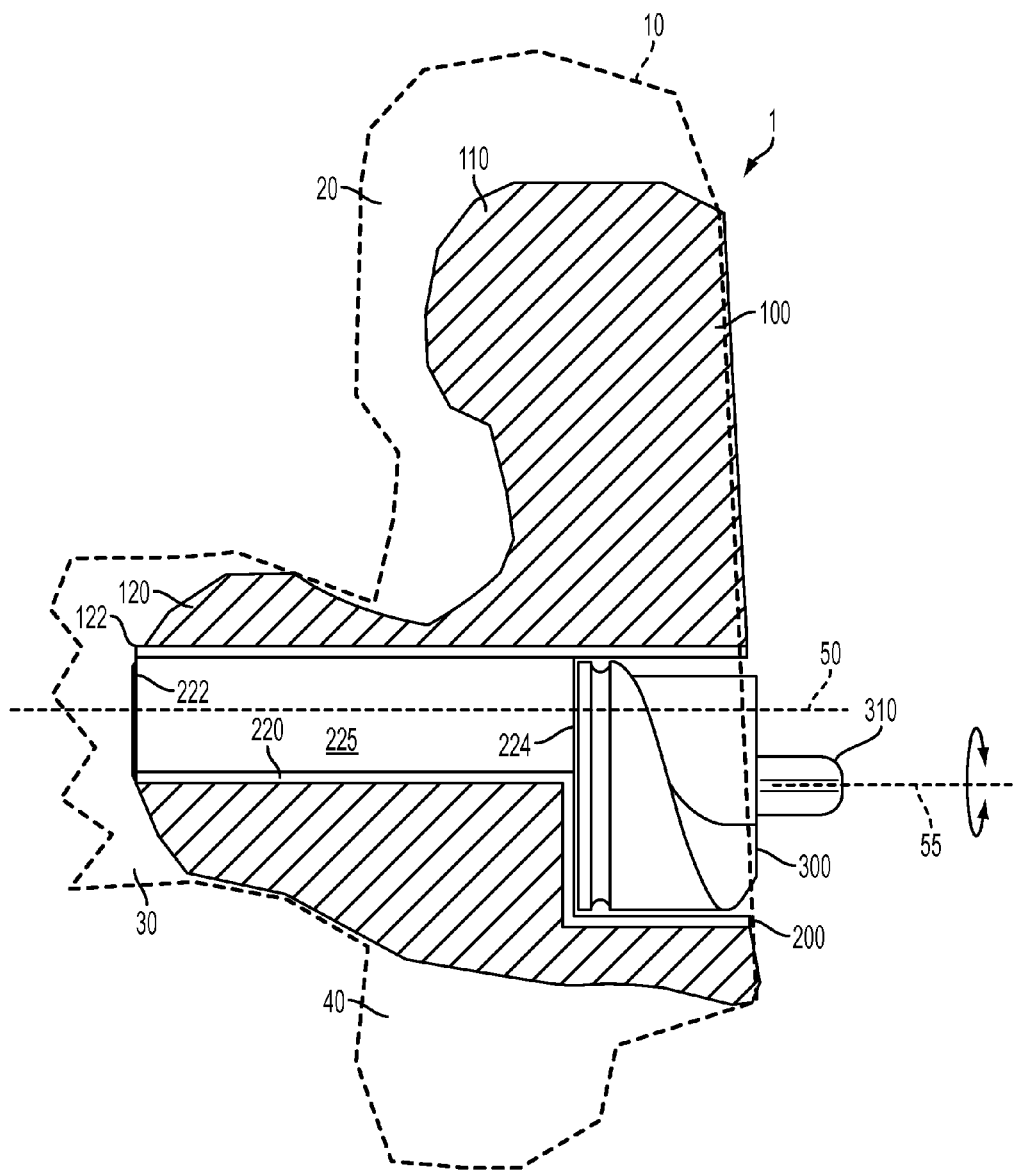
FIG. 2 is a cross-sectional plan view of the hearing protection device of FIG. 1 showing also the outline of an ear into which the hearing protection device is inserted.
Figure 3:
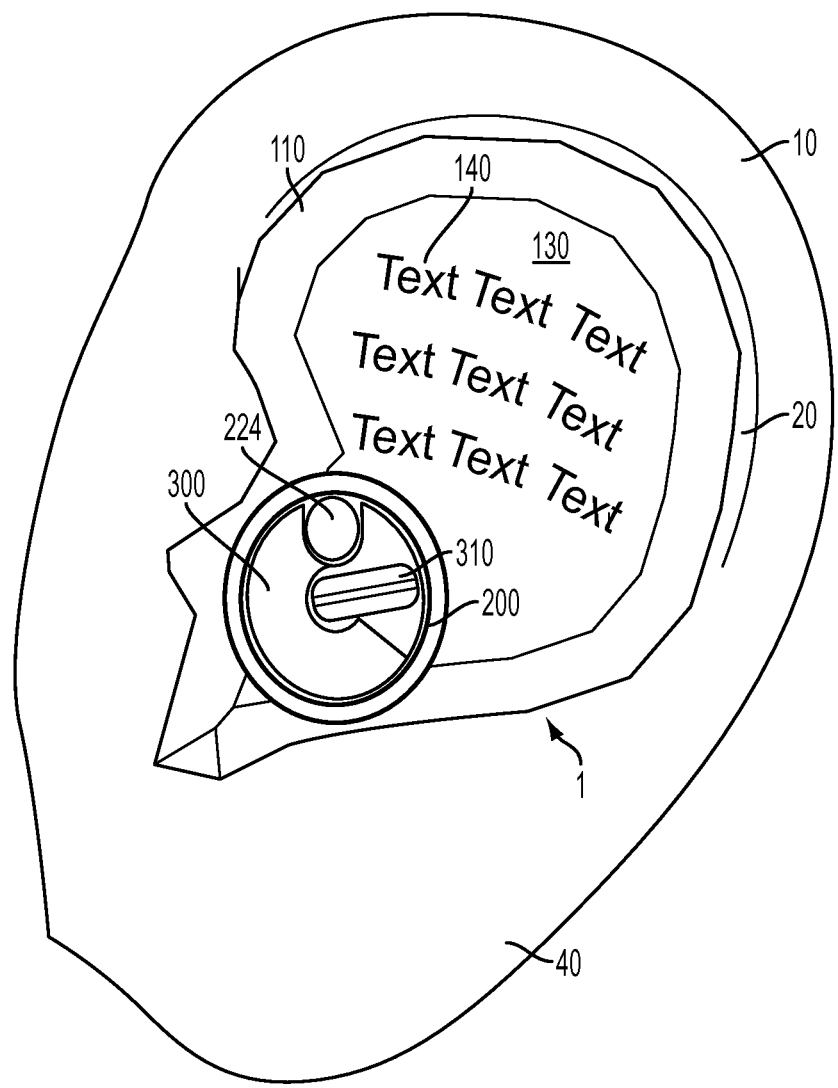
FIG. 3 is a perspective view of a human ear in which a hearing protection device according to embodiments described herein is worn.

Referring to FIGS. 1-3, a hearing protection device 1 according to some embodiments may include an earplug body 100 and an adjustable sound attenuation assembly. The earplug body 100 may include a canal portion 120 that is insertable into an ear canal 30 of an ear 10. The earplug body 100 may also include a canal opening 122 at a proximal end of the canal portion 120 that opens into the ear canal 30 when the canal portion 120 is inserted into the ear canal 30. In some embodiments, as shown in FIG. 2, the canal opening 122 may be flush with the proximal opening 222 of the attenuator case 200. The earplug body may also include an outer portion 110 that is disposed in the concha bowl 20 of the ear 10 when the canal portion 120 is inserted into the ear canal 30. The adjustable sound attenuation assembly includes two main components: an attenuator case 200 disposed in the earplug body 100, and an attenuator insert 300 that is removably insertable into the attenuator case 200.

Referring to FIGS. 1-3, 4A, and 4B, as a component of the adjustable sound attenuation assembly, the attenuator case 200 includes a hollow barrel portion 210 that accommodates the attenuator insert 300. The attenuator case 200 also includes a hollow extension portion 220 connected to the hollow barrel portion 210. The hollow extension portion 220 of the attenuator case 200 is disposed in the canal portion 120 of the earplug body 100. The hollow extension portion 220 has a soundpath channel 225 defined through the hollow extension portion 220. The soundpath channel 225 has a distal opening 224 into the hollow barrel portion 210 and a proximal opening 222 opposite the distal opening 224. The soundpath channel 225 defines a soundpath axis 50 (FIG. 2).

Figure 5:
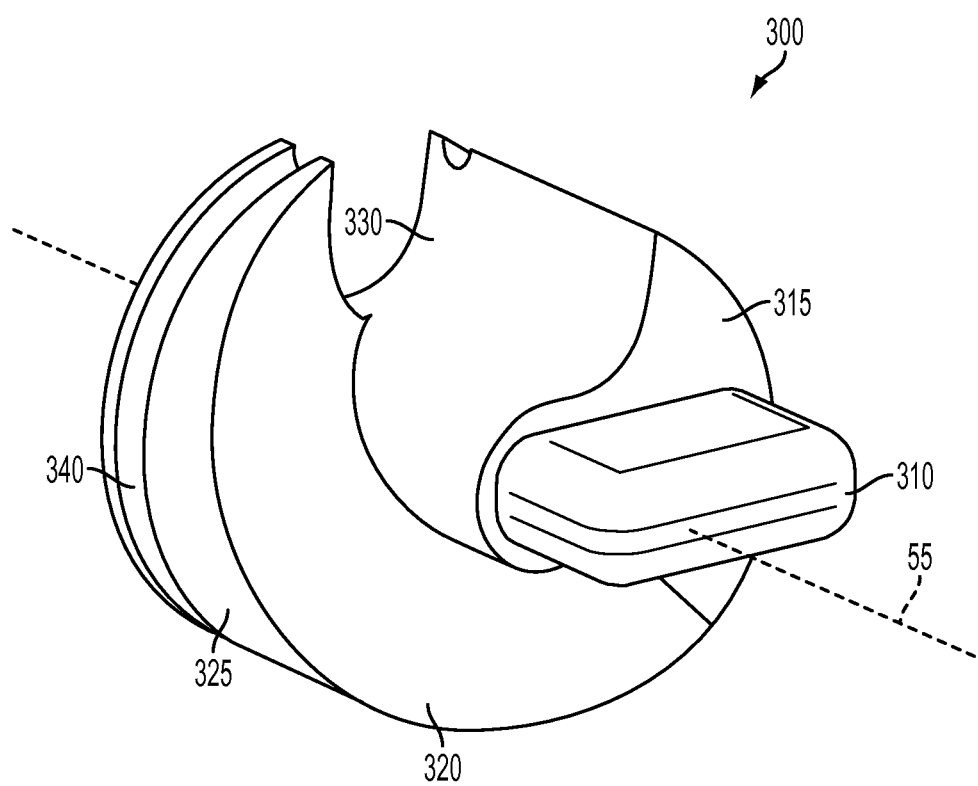
FIG. 5 is a perspective view of an attenuator insert, a component of hearing protection devices according to embodiments described herein.

Referring to FIGS. 1-3 and 5, the attenuator insert 300 is rotatable within the hollow barrel portion 210 of the attenuator case 200 about an insert rotation axis 55 (FIGS. 2 and 5). In some embodiments, the insert rotation axis 55 is noncollinear with the soundpath axis 50 defined by the soundpath channel 225 of the attenuator case 200. As will be described in greater detail below, the attenuator insert 300 has a thickness along the soundpath axis 50 that varies with respect to a rotation angle θ of the attenuator insert 300 within the attenuator case 200. Thereby, sound waves that enter the soundpath channel 225 through the distal opening 224 of the attenuator case 200 are attenuated proportionally to the thickness of the attenuator insert 300 along the soundpath axis 50.

Having described in general various components of hearing protection devices according to some embodiments, the various components, particularly the earplug body 100, the attenuator case 200, and the attenuator insert 300 according to various embodiments will now be described in greater detail.

Referring to FIGS. 1-3, the earplug body 100 of the hearing protection device 1 may be adapted to the shape of the ear 10 of the intended user or wearer. For reference, the ear 10 of FIGS. 2 and 3 is intended to be exemplary of the general population and includes a concha bowl 20, an ear canal 30 that extends into the head toward an ear drum (not shown), and an ear lobe 40. In particular, the earplug body 100 may be adapted such that the outer portion 110 fits comfortably in the concha bowl 20 of the ear 10 and the canal portion 120 fits comfortably in the ear canal 30 of the ear 10. Additionally, in some embodiments the earplug body 100 may be adapted to retain the hearing protection device 1 in the ear 10 without the aid of an attachment device and without the exertion of force from an external source. In some embodiments, the outer portion 110 may have a concha shape that may be designed to fit into the concha bowl of ears of the general population. The canal portion 120 may also have an ear canal shape that may be designed to fit into the ear canal found in the general population. In some embodiments, the outer portion 110, the canal portion 120, or both may be custom made from a mold of the actual concha bowl or ear canal of the intended wearer. Such a custom fitting of the earplug body 100 may aid retention of hearing protection device 1 in the ear 10. The canal portion 120 may be further adapted to provide a proper sealing of the ear canal 30 so that all sounds that enter the ear canal 30 from the environment directly into the ear canal 30 do so through only the soundpath channel 225 of the attenuator case 200. It should be understood that inevitably some sound waves may travel into the ear canal 30 indirectly, such as through bone or other parts of the anatomy, and that blocking of such sound waves is not possible using only any hearing protection device that is inserted into the ear canal 30.

The earplug body 100 may include or be formed from rigid or soft and pliable material suitable for dampening or attenuating sound volume to a level that reduces or eliminates damage to the cochlea, ear drum, or the entire auditory system. Examples of suitable materials for the material body include, without limitation: compressible foams, elastomeric polymers, plastics, surgical-grade rubbers, or any other rubber that reduces vibrations. The earplug body 100 may be a solid piece of material (as shown in FIG. 1, for example) or may be a skeleton framework having the basic structure shown in FIG. 1 but missing portions of material not required to support the earplug body 100 in the concha bowl 20 of the wearer.

In some embodiments, the outer portion 110, the canal portion 120, or both may be shaped to fit into the specific wearer's ear through the use of a trimming device such as scissors or a knife, for example. For this purpose, outer portion 110 of the earplug body 100, the canal portion 120 of the earplug body 100, or both, may include cuttable portions for custom sizing of the hearing protection device 1 for a wearer of the hearing protection device 1. For example, portions of the outer portion 110 farthest away from the attenuator case 200 may be trimmable or cuttable to fit a smaller concha bowl of a child or small adult. Likewise, portions of the canal portion 120 that extend deepest into the ear canal 30 may be trimmable or cuttable to fit a shorter ear canal of a child or small adult.

The earplug body 100 may include an outer surface 130 that may be visible from outside the ear 10 and is directly exposed to unattenuated sound from the environment. In some embodiments, the outer surface 130 of the earplug body 100 may be decorated with customized indicia 140. The customized indicia may include text, company trademarks, logos, pictures, words, or any combination thereof, for example. The customized indicia 140 may be added to the outer surface 130 by any practical method such as embossing, engraving, adhering with glue or epoxy, or by attaching a separate piece of material (not shown) including the customized indicia 140 thereon. In some embodiments, the customized indicia 140 may be added to the outer surface 130 of the earplug body 100 when the earplug body 100 is molded, such as by selecting various colors of materials for the earplug body 100 or by in-mold labeling, for example.

In some embodiments, the hearing protection device 1, particularly the earplug body 100, may additionally include a placard (not shown) mounted on the outer surface 130 of the earplug body 100, and the placard may include the customized indicia 140 thereon. The placard may be removably or permanently mounted to the outer surface 130 in a mounting hole (not shown) on the outer surface 130, for example. Such a placard may be of any size and shape. If the placard is removably mounted to the outer surface 130, for example, the placard may be exchanged with a second placard having different customized indicia 140 thereon by removing the placard and mounting the second placard.

As described above, the hearing protection device 1 includes the adjustable sound attenuation assembly, which includes the attenuator case 200 and the attenuator insert 300. Referring to FIGS. 1, 2, 4A, and 4B, the attenuator case 200 will now be described. During use of the hearing protection device 1, the adjustable sound attenuation assembly is disposed in the earplug body 100. Though in some embodiments the attenuator insert 300 may be removable from the attenuator case 200, the attenuator case 200 itself may be permanently secured in the earplug body 100 by an adhesive, a friction fit, an epoxy, a weld, or similar means. In illustrative embodiments, the earplug body 100 may be molded around the attenuator case 200 when the earplug body 100 is formed. Though in some embodiments the attenuator case 200 may be permanently secured in the earplug body 100, it is contemplated that the earplug body 100 may also be molded first, then a bore of suitable size to accommodate the attenuator case 200 may be drilled into the earplug body 100, and the attenuator case 200 may be inserted permanently or removably into the bore. Suitable materials for the attenuator case 200 may include rigid or elastomeric materials such as plastics or rubbers. In some embodiments, the attenuator case 200 may be constructed of a material that is harder or more rigid than the material from which the attenuator insert 300 is constructed.

Figure 4A:
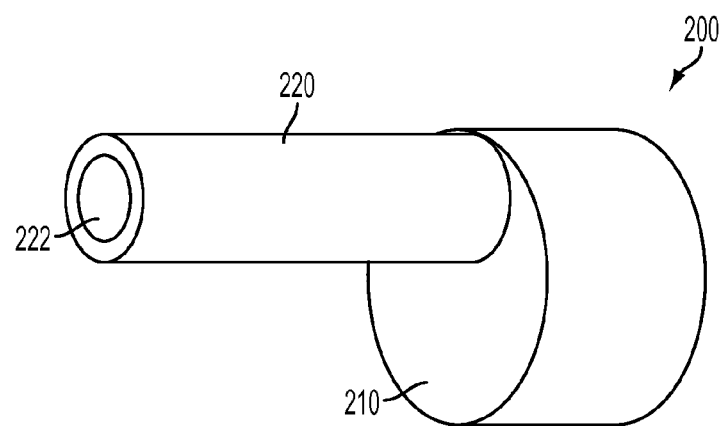
FIG. 4A is a perspective view of an attenuator case, a component of hearing protection devices according to embodiments described herein.
Figure 4B:
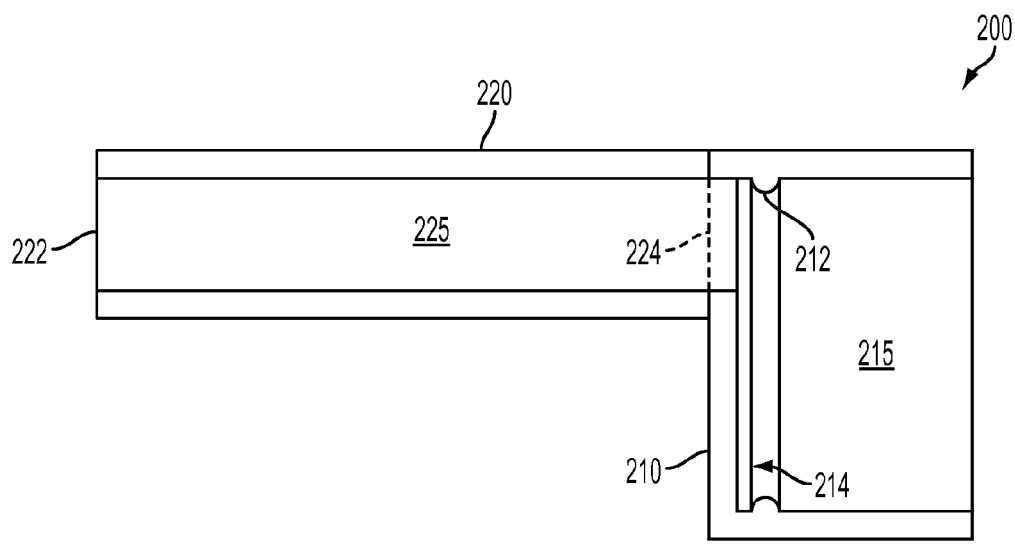
FIG. 4B is a cross-sectional plan view of the attenuator case of FIG. 4A.

As shown in the embodiment of FIGS. 4A and 4B, the attenuator case 200 may include a hollow barrel portion 210 that accommodates the attenuator insert 300 therein. In some embodiments, the hollow barrel portion 210 of the attenuator case 200 may be substantially cylindrical. The attenuator case 200 may also include a hollow extension portion 220 connected to the hollow barrel portion 210. The hollow extension portion 220 of the attenuator case 200 may be disposed in the canal portion 120 of the earplug body 100. In some embodiments, the hollow extension portion 220 of the attenuator case 200 may be substantially cylindrical. The outside diameter of the hollow extension portion 220 may be chosen to enable filling the maximum practical portion of the ear canal 30 of the intended wearer while still providing comfort to the wearer and also providing a suitable seal against external sounds. The inside diameter of the hollow extension portion 220, particularly of the soundpath channel 225 may be chosen to be sufficiently large such that it the quality, integrity, and/or clarity of sound entering the soundpath channel 225 are substantially unaffected. In some embodiments, the attenuator case 200 may be a unitary piece without joints or seals and may be formed by a single molding process, for example. In other embodiments, the hollow barrel portion 210 may be attached to the hollow extension portion 220 by an adhesive, an epoxy, a weld, or similar joining means.

The hollow extension portion 220 of the attenuator case 200 has a soundpath channel 225 defined therethrough from a distal opening 224 into the hollow barrel portion 210 to a proximal opening 222 opposite the distal opening 224. In some embodiments, as shown in FIG. 2, the canal opening 122 of the earplug body 100 may be flush with the proximal opening 222 of the attenuator case 200. In other embodiments, the hollow extension portion 220 may extend beyond the canal opening 122 of the earplug body 100 and into the ear canal 30. In other embodiments, the hollow extension portion 220 may not extend to the canal opening 122, such that the distal opening 244 and the soundpath channel 225 of the attenuator case 200 open into the earplug body 100 without opening directly into the ear canal 30. The soundpath channel 225 defines a soundpath axis 50. The inside diameter of the hollow extension portion 220, particularly of the soundpath channel 225 may be chosen to be sufficiently large such that it the quality, integrity, and/or clarity of sound entering the soundpath channel 225 are substantially unaffected.

In some embodiments, the distal opening 224 of the soundpath channel 225 is not concentric with the hollow barrel portion 210 of the attenuator case 200. That is, the distal opening 224 may be off-center from the hollow barrel portion 210. In such embodiments, the soundpath axis 50 will not be collinear with the insert rotation axis 55 of the attenuator insert 300, because the insert rotation axis 55 may extend through the center point of the hollow barrel portion 210. Though the attenuator case 200 may be included in the earplug body 100 in any orientation, not limited to the orientation shown in FIGS. 1-3, for example, in preferred embodiments, the attenuator case 200 may be configured such that the soundpath axis 50 is above the insert rotation axis 55 when the canal portion 120 of the earplug body 100 is inserted into the ear canal 30. Thereby, it is believed that the soundpath axis 50 may extend out of the hearing protection device 1 toward the ear drum, for example, through an upper portion of the ear canal 30. Because common obstructions to the ear canal 30 such as earwax (cerumen) often deposit at the bottom of the ear canal 30, drawn there by gravity, aiming the soundpath axis 50 through an upper portion of the ear canal 30 may minimizes intersection of the soundpath axis 50 with such obstructions in the lower portion of the ear canal 30.

In some embodiments, the attenuator case 200 may include a case protrusion 212 inside the hollow barrel portion 210. The case protrusion 212 may be a continuous ring inside the hollow barrel portion 210 as shown in FIG. 4B or may include one or more tabs or bumps. The case protrusion 212 may be configured to engage a suitable feature on the attenuator insert 300 such as a retaining groove 340 (see FIG. 5, for example) and thereby secure the attenuator insert 300 into the attenuator case 200 when the attenuator insert 300 is removably inserted into the attenuator case 200. When a case protrusion 212 and a retaining groove 340 are present, the user of the hearing protection device 1 may experience a snapping sound when the attenuator insert 300 is inserted into the attenuator case 200 as an assurance that the attenuator insert 300 has been correctly inserted.

Referring to FIGS. 5-9, the attenuator insert 300 will now be described. Various perspective views of the attenuator insert 300 are provided in FIGS. 5, 8 and 9. Operation of the attenuator insert 300 within the attenuator case 200 will be described below with reference to FIGS. 10A-13B.

According to some embodiments, the attenuator insert 300 may be a generally round body adapted to fit into the attenuator case 200, particularly the hollow barrel portion 210 of the attenuator case 200. The attenuator insert 300 may be rotatable within the hollow barrel portion 210 of the attenuator case 200 about an insert rotation axis 55. As described above with regard to avoiding intersection of the soundpath axis 50 with obstructions such as cerumen deposits, in some embodiments, the insert rotation axis is not collinear with the soundpath axis 50. In embodiments for which the hollow barrel portion 210 is substantially cylindrical, the attenuator insert 300 may have a substantially circular cross section perpendicular to the insert rotation axis 55. In some embodiments, the attenuator insert 300 may include a handle 310 that the wearer of the hearing protection device 1 may use to rotate the attenuator insert 300 within the attenuator case 200 and adjust the sound attenuation level of the hearing protection device 1.

The attenuator insert 300 may be made from any material that attenuates the volume of sound as a function of the thickness of the material between the source of the sound and the place where the sound will be detected (the ear drum, for example). In some embodiments, the attenuator insert 300 may be a one-piece construction of a single material. In other embodiments, the attenuator insert 300 may be made from more than one material. For example, the handle 310 may be made from a harder material than the rest of the attenuator insert 300. In some embodiments, the attenuator insert 300 may be formed from any material that reduces vibrations caused by incoming sound waves. Suitable materials in this regard include polymers, foams, plastics, and rubbers such as surgical-grade rubbers.

As described above, attenuator insert 300 may include a retaining groove 340 that engages a corresponding feature of the attenuator case 200, such as a case protrusion 212 (FIG. 4B), for example, that secures the attenuator insert 300 into the attenuator case 200 when the attenuator insert 300 is inserted into the attenuator case 200. In some embodiments, the retaining groove 340 may be configured to enable the attenuator insert 300 to rotate a full 360° within the attenuator case 200. In other embodiments not shown, the retaining groove 340 may include one or more stops that prevent the attenuator insert 300 from being turned a full 360° within the attenuator case 200. It is also contemplated that the attenuator insert 300 may include a protrusion and the attenuator case 200 may include a groove and that such a modification is in all regards equivalent to the embodiment in which the attenuator insert 300 includes the retaining groove 340 and the attenuator case 200 includes the case protrusion 212.

The attenuator insert 300 may have a thickness along the soundpath axis 50 that varies with respect to a rotation angle θ of the attenuator insert 300 within the attenuator case 200. The variable thickness is illustrated structurally in FIGS. 5-9 and in operation in FIGS. 10A-13B. In some embodiments, the thickness of the attenuator insert 300 along the soundpath axis 50 may be defined by a distance from a flat proximal end 350 (FIG. 8) of the attenuator insert 300 along a lateral wall 325 of the attenuator insert 300 to a sloped distal surface 320 of the attenuator insert 300. In some embodiments, the sloped distal surface 320 may have a gradual slope from a zero-attenuation groove 330 of the attenuator insert 300 to a maximum attenuation portion 315 of the attenuator insert 300. Thereby, the thickness of the lateral wall 325 may increase gradually and proportionately to the steepness of the slope of the sloped distal surface 320.

Figure 6:
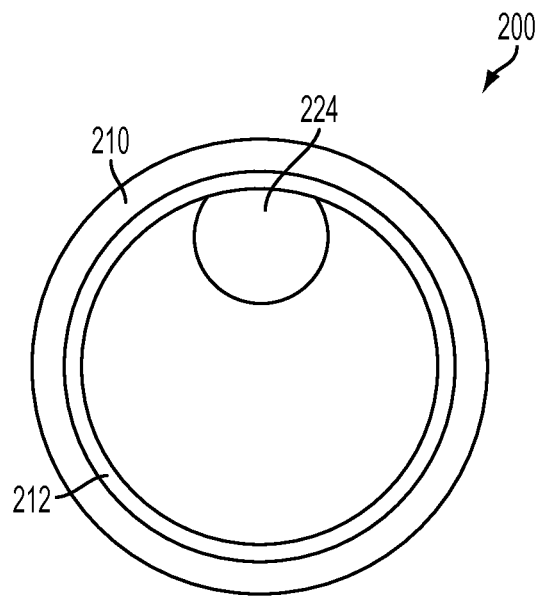
FIG. 6 is an end view of the attenuator case of FIG. 4A.
Figure 7:
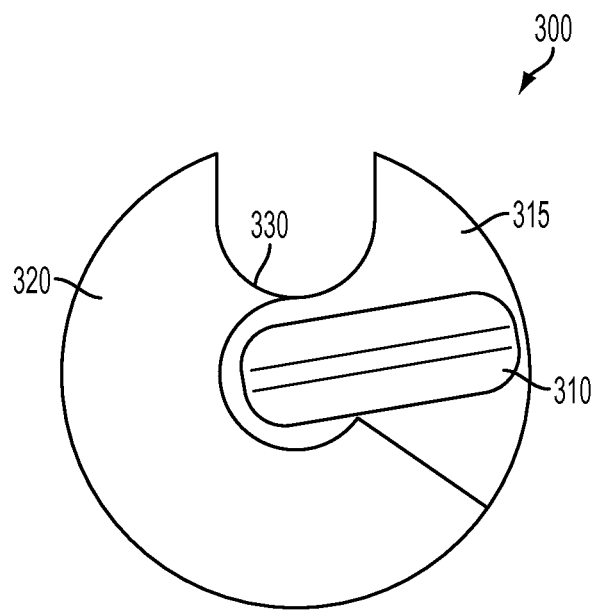
FIG. 7 is a top view of the attenuator insert of FIG. 6.
Figure 8:
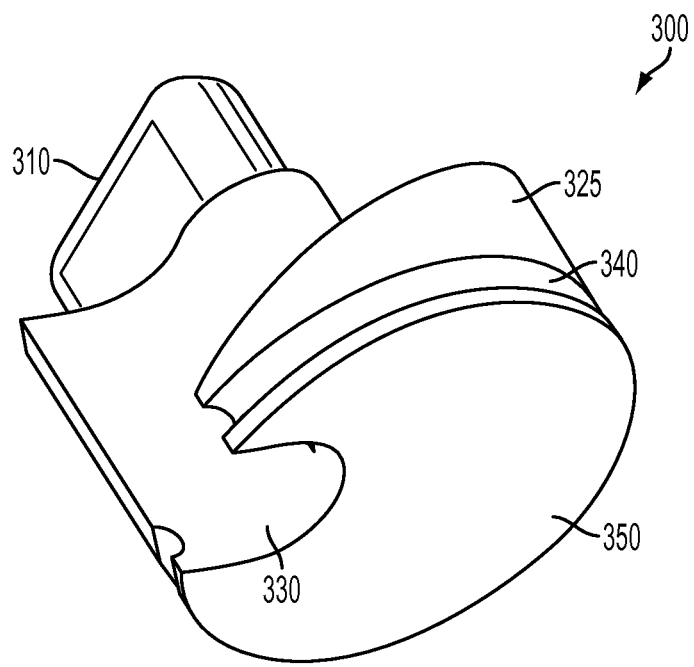
FIG. 8 is a bottom-side perspective view of the attenuator insert of FIG. 6.
Figure 9:
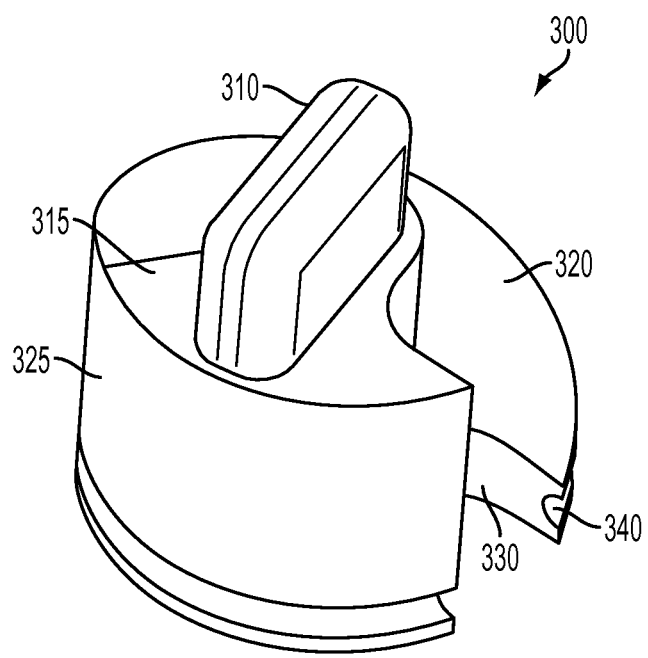
FIG. 9 is a side perspective view of the attenuator insert of FIG. 6.

When present, the zero-attenuation groove 330 may represent the lowest amount of attenuation possible (zero or nearly zero) for the attenuator insert 300. The maximum attenuation portion 315 (i.e., the thickest portion of the attenuator insert 300) may represent the greatest amount of attenuation possible for the attenuator insert 300. In FIGS. 5 and 6, top views of the attenuator case 200 and the attenuator insert 300 are provided in an orientation that demonstrates how the zero-attenuation groove 330 of the attenuator insert 300 may align with the distal opening 224 of the attenuator case 200 such that sound waves may enter the distal opening 224 unimpeded by the attenuator insert 300 and, therefore, substantially unattenuated.

In each of FIGS. 10A, 11A, 12A, and 13A, an attenuator insert 300 is shown in a certain rotational orientation with respect to the insert rotation axis 55 of the attenuator insert (see FIG. 5), with the handle 310 oriented upward. Visible features of the attenuator insert 300 may include the handle 310, the sloped distal surface 320, the lateral wall 325, the zero-attenuation groove 330, and the retaining groove 340. In each figure, the soundpath axis 50 is depicted for reference in front of the attenuator insert 300. In corresponding FIGS. 10B, 11B, 12B, and 13B, a top view of an adjustable sound attenuation assembly 400 is shown, which includes the attenuator insert 300 within the attenuator case 200. In these figures, visible elements of the attenuator insert 300 include the handle 310, the maximum attenuation portion 315, the sloped distal surface 320, and the zero-attenuation groove 330. Depending on the orientation of the attenuator insert 300, in each figure the distal opening 224 is shown as either visible (FIG. 10B) or as hidden underneath the attenuator insert 300 (FIGS. 11B, 12B, and 13B).

Figure 10A:
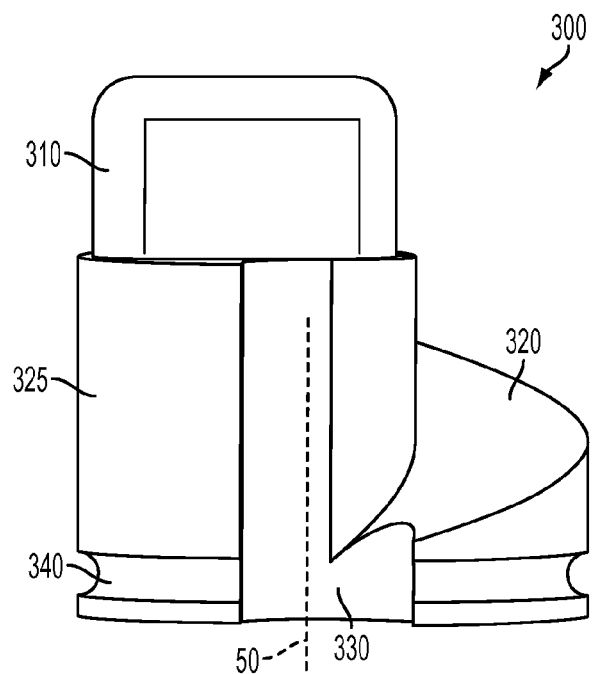
FIG. 10A is a perspective view of the attenuator insert of FIG. 6 showing a zero-attenuation groove.
Figure 10B:
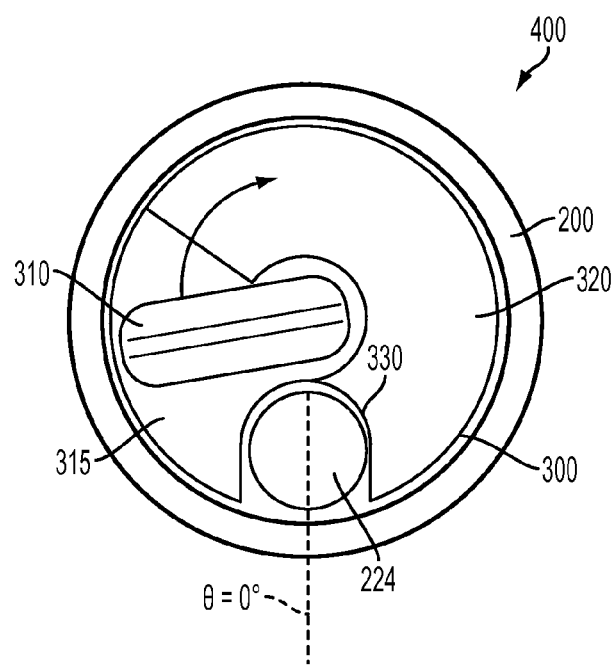
FIG. 10B is a top view of the attenuator insert of FIG. 6 oriented as in FIG. 10A and inserted into an attenuator case to show relative positions of the attenuator insert with respect to a soundpath channel in the attenuator case.

FIGS. 10A and 10B illustrate a minimum-attenuation or zero-attenuation position of the attenuator insert 300 relative to the distal opening 224 of the attenuator case 200. In this position, the attenuator insert 300 includes the zero-attenuation groove 330 defining a rotation angle of 0°, at which the zero-attenuation groove 330 is disposed over the distal opening 224. When the rotation angle is 0°, the thickness of the attenuator insert 300 along the soundpath axis 50 is zero, and sound waves that enter the soundpath channel 225 (see FIG. 4B) through the distal opening 224 are unattenuated by the attenuator insert 300.

Figure 11A:
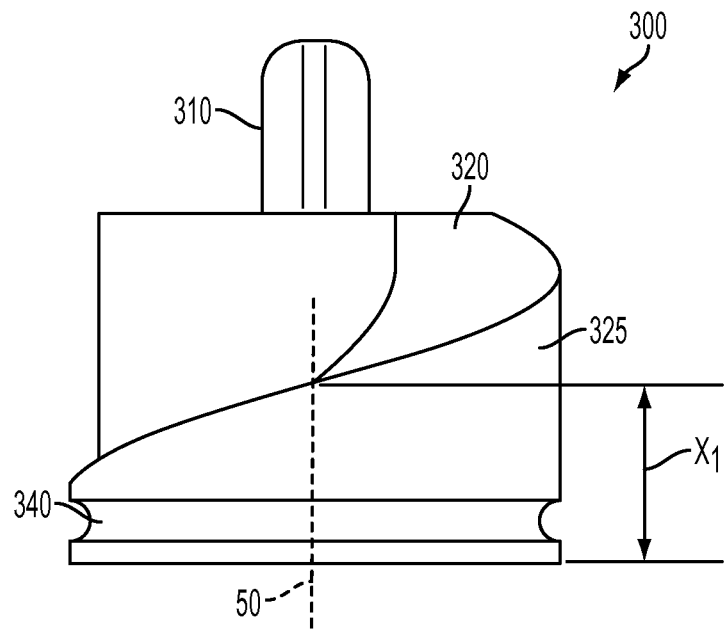
FIG. 11A is a perspective view of the attenuator inserts of FIGS. 6 and 10A rotated about a rotation axis of the attenuator insert to show increasing thickness of the attenuator insert with respect to the rotation.
Figure 11B:
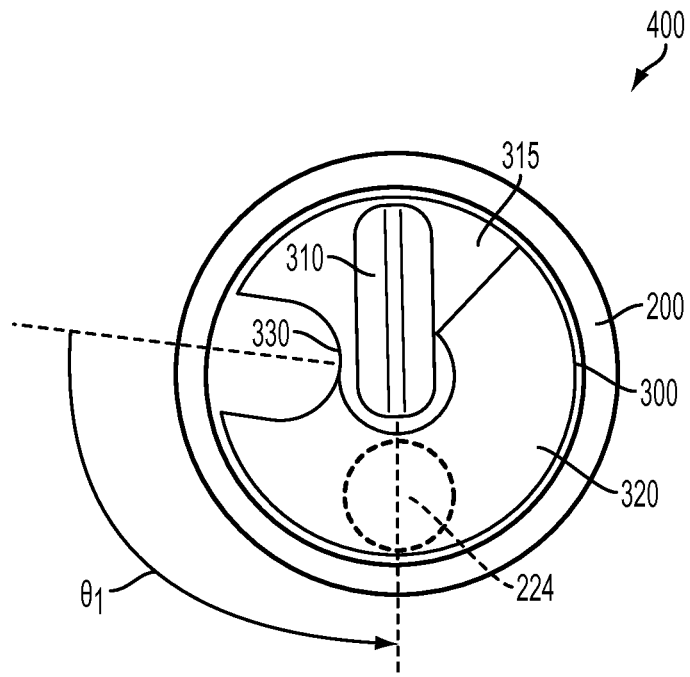
FIG. 11B is a top view of the attenuator insert of FIG. 6 oriented as in FIG. 11A and inserted into an attenuator case to show relative positions of the attenuator insert with respect to a soundpath channel in the attenuator case.

FIGS. 11A and 11B illustrate a first attenuated position of the attenuator insert 300 relative to the distal opening 224 of the attenuator case 200. In this position, the zero-attenuation groove 330 is rotated (clockwise as shown, but may be counterclockwise) through a rotation angle of $\theta_1$ relative to the distal opening 224 of the attenuator case 200. In this position, an attenuating thickness $x_1$ of the attenuator insert 300 is disposed over the distal opening 224, such that sound waves that enter the soundpath channel 225 (see FIG. 4B) through the distal opening 224 attenuated by an amount proportional to the attenuating thickness $x_1$.

Figure 12A:
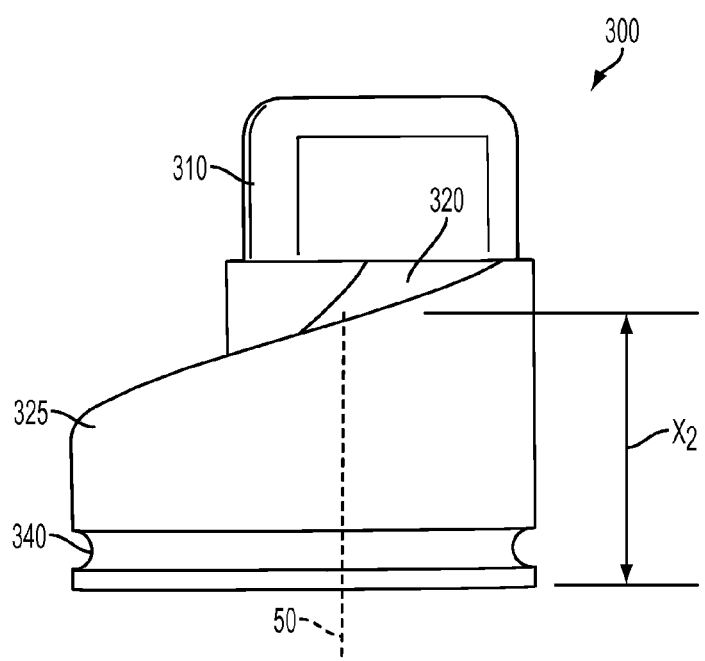
FIG. 12A is a perspective view of the attenuator inserts of FIGS. 6 and 11A further rotated about the rotation axis of the attenuator insert to show increasing thickness of the attenuator insert with respect to the further rotation.
Figure 12B:
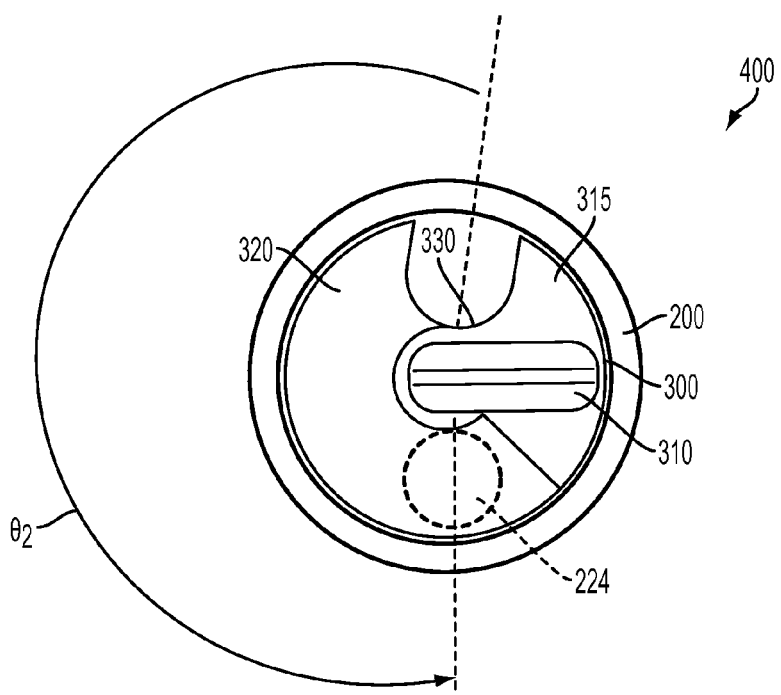
FIG. 12B is a top view of the attenuator insert of FIG. 6 oriented as in FIG. 12A and inserted into an attenuator case to show relative positions of the attenuator insert with respect to a soundpath channel in the attenuator case.

FIGS. 12A and 12B illustrate a second attenuated position of the attenuator insert 300 relative to the distal opening 224 of the attenuator case 200. In this position, the zero-attenuation groove 330 is rotated (clockwise as shown, but may be counterclockwise) through a rotation angle of $\theta_2 > \theta_1$ relative to the distal opening 224 of the attenuator case 200. In this position, an attenuating thickness $x_2 > x_1$ of the attenuator insert 300 is disposed over the distal opening 224, such that sound waves that enter the soundpath channel 225 (see FIG. 4B) through the distal opening 224 attenuated by an amount proportional to the attenuating thickness $x_2$, which is greater than the attenuation achieved at the attenuating thickness $x_1$ in the position shown in FIGS. 11A and 11B. In general, it should be understood that as the thickness of the attenuating material of the attenuator insert 300 covering the distal opening 224 of the attenuator case 200 increases, the attenuation of sound from the environment increases proportionally.

Figure 13A:
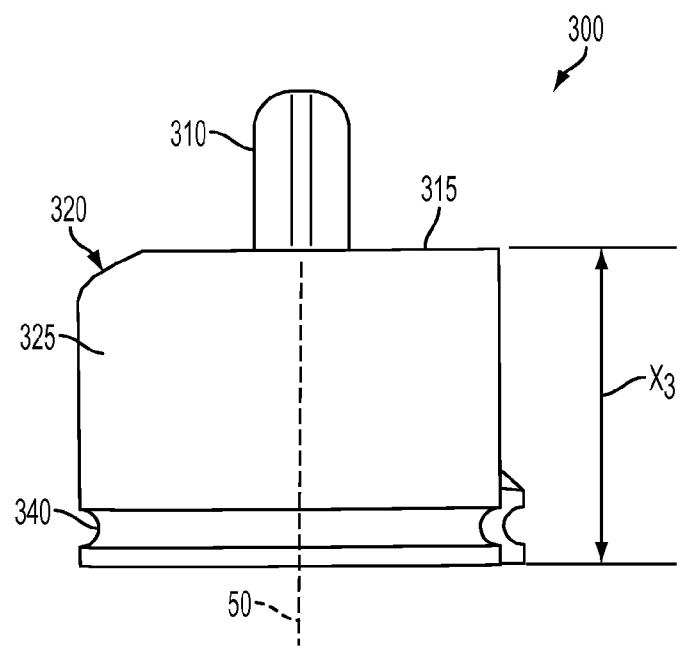
FIG. 13A is a perspective view of the attenuator inserts of FIGS. 6 and 12A further rotated about the rotation axis of the attenuator insert to show a position of maximum attenuation of the attenuator insert with the further rotation to a maximum attenuation angle.
Figure 13B:
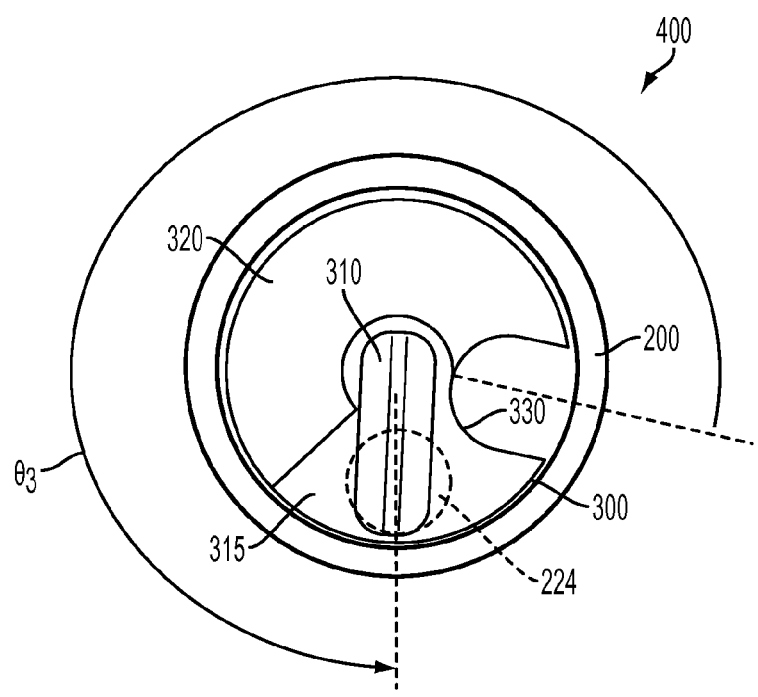
FIG. 13B is a top view of the attenuator insert of FIG. 6 oriented as in FIG. 13A and inserted into an attenuator case to show relative positions of the attenuator insert with respect to a soundpath channel in the attenuator case.

FIGS. 13A and 13B illustrate a maximum attenuated position of the attenuator insert 300 relative to the distal opening 224 of the attenuator case 200. In this position, the zero-attenuation groove 330 is rotated (clockwise as shown, but may be counterclockwise) through a maximum attenuation rotation angle of $\theta_3 > \theta_2 > \theta_1$ relative to the distal opening 224 of the attenuator case 200. In this position, an attenuating thickness $x_3 > x_2 > x_1$ of the attenuator insert 300 is disposed over the distal opening 224, such that sound waves that enter the soundpath channel 225 (see FIG. 4B) through the distal opening 224 attenuated by an amount proportional to the attenuating thickness $x_3$, which is greater than the attenuation achieved at the attenuating thickness $x_2$ in the position shown in FIGS. 12A and 12B and also greater than the attenuating thickness $x_1$ in the position shown in FIGS. 11A and 11B. In particular, in the position shown in FIGS. 13A and 13B, the maximum attenuation portion 315 of the attenuator insert 300 is disposed over the distal opening 224 of the attenuator case 200.

It should be understood that the attenuator insert 300 may be rotated either clockwise or counterclockwise within the attenuator case 200. As such, it should be understood that the position of maximum attenuation shown in FIGS. 13A and 13B may also be achieved by rotating the attenuator insert 300 counterclockwise through a rotation angle of $360° - \theta_3$ instead of clockwise through a rotation angle of $\theta_3$. In some embodiments, the thickness of the attenuator insert 300 along the soundpath axis 50 increases gradually as the attenuator insert 300 is rotated in a first direction (clockwise, for example) from the rotation angle of 0° to a maximum attenuation rotation angle and increases abruptly as the attenuator insert is rotated in a second direction (counterclockwise, for example) opposite the first direction from the rotation angle of 0° to the maximum attenuation rotation angle. In some embodiments, the maximum attenuation rotation angle is less than 270° relative to the rotation angle of 0° in the first direction. In other embodiments (as in FIGS. 13A and 13B), the maximum attenuation rotation angle is less than 90° relative to the rotation angle of 0° in the second direction. It is believed that minimizing the maximum attenuation rotation angle may add convenience to the hearing protection device 1, because a small maximum attenuation rotation angle may enable the user or wearer of the hearing protection device 1 to switch from zero attenuation to maximum attenuation with minimal time and effort.

In some embodiments not shown in the figures, the attenuator insert 300 may lack a zero-attenuation groove 330 but may include a minimum attenuation portion representing a minimum but non-zero attenuation. In other embodiments contemplated but not shown, the sloped distal surface 320 may be configured not as a gradual slope but as a plurality of stepped surfaces that may increase in one rotational direction or may alternate from thick to thin multiple time within one rotation of the attenuator insert 300. Stepped surfaces may be configured to increase the attenuation of the volume of sound in set increments as the thickness of each step of the plurality of stepped surfaces increases.

Having described various embodiments of hearing protection devices above, various embodiments of hearing protection kits will now be described with general reference to FIGS. 1-5. According to some embodiments, the hearing protection kits may include at least one earplug body 100 having an attenuator case 200 therein and may also include at least one attenuator insert 300. Each earplug body 100 in the hearing protection kits may include a canal portion 120 that is insertable into an ear canal 30 of an ear 10; a canal opening 122 at a proximal end of the canal portion 120 that opens into the ear canal 30 when the canal portion 120 is inserted into the ear canal 30; and an outer portion 110 that is disposed in the concha bowl 20 of the ear 10 when the canal portion 120 is inserted into the ear canal 30. The attenuator case 200 disposed in the earplug body 100 may include a hollow barrel portion 210 that accommodates the attenuator insert 300 therein; and a hollow extension portion 220 connected to the hollow barrel portion 210. The hollow extension portion 220 of the attenuator case 200 may be disposed in the canal portion 120 of the earplug body 100. The hollow extension portion 220 has a soundpath channel 225 defined therethrough. The soundpath channel 225 has a distal opening 224 into the hollow barrel portion 210 and a proximal opening 222 opposite the distal opening 224. The soundpath channel 225 may define a soundpath axis 50.

Each attenuator insert 300 in the hearing protection kits may rotatable within the hollow barrel portion 210 of the attenuator case 200 in the earplug body 100 about an insert rotation axis 55. The insert rotation axis 55 may be noncollinear with the soundpath axis 50. The at least one attenuator insert 300 may have a thickness along the soundpath axis 50 that varies with respect to a rotation angle $\theta$ of the at least one attenuator insert 300 within the attenuator case 200 in the at least one earplug body 100. The at least one attenuator insert 300 may have a maximum thickness along the soundpath axis 50 that defines a maximum attenuation of the at least one attenuator insert 300.

When the kit is assembled with the at least one attenuator insert 300 being inserted into the attenuator case 200 of the at least one earplug body 100, sound waves that enter the soundpath channel 225 through the distal opening 224 may be attenuated proportionally to the thickness of the attenuator insert 300 along the soundpath axis 50.

In some embodiments, the hearing protection kits may include a plurality of attenuator inserts. In some embodiments, the plurality of attenuator inserts may include multiple attenuator inserts each having the same maximum attenuation so that additional attenuator inserts may be used as replacements or backups. In other embodiments, the plurality of attenuator inserts may include an assortment of attenuator inserts having different maximum attenuations so that a wearer can select the amount of protection needed based on expected exposure to noises or loud environmental sounds.

In some embodiments, the hearing protection kits may include at least one earplug body 100 having an outer surface 130 that is decorated with customized indicia 140. In some embodiments, the hearing protection kits may include at least one placard that is mountable on the outer surface 130 of the at least one earplug body 100, and the placard may include the customized indicia 140 thereon. In some embodiments, the at least one placard may include multiple placards with different customized indicia thereon, so that a wearer can choose a placard based on occasion or need. In some embodiments, the placard may be brightly colored for use as a safety device. In other embodiments, the placard may include an advertisement, a message, or a trademark. For example, customized placards may be manufactured with indicia including a block numeral for the pit crew of a race car driver who drives a car with the same number as the block numeral.

In other embodiments, hearing protection kits may further include an electronic device such as a speaker or a listening device such as an earbud that is adapted to fit within the attenuator case 200 in the place of the attenuator insert 300. Such embodiments may illustrate convenience and versatility of the hearing protection devices described herein, in that the attenuator case 200 may function as an inlet port for modular inserts not limited to the attenuator insert 300. When a speaker or listening device is inserted into the attenuator case 200, the earplug body 100 of the hearing protection device 1 may continue to attenuate the volume of sound from the environment and may allow the user or wearer to monitor the sound in the speaker or listening device.

Thus, hearing protection devices and kits containing the hearing protection devices have been described. The hearing protection devices according to embodiments herein are mechanically simple and lack electronic circuitry yet may be quickly and easily adjusted to provide variable levels of sound attenuation. The hearing protection devices and kits may be well suited for use by the general population or by wearers who have particular needs to hear in low-noise environments that can quickly change to high-noise environments but who may be averse to constantly removing and reinserting hearing protection throughout the day as the noise levels change.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Though specific embodiments have been described herein, it should be apparent that modifications and variations are possible without departing from the scope of the appended claims. More specifically, although some embodiments herein may be identified as preferred or particularly advantageous, preference for such embodiments is not contemplated to imply limitation to the preferred embodiments.

What is claimed is:

1. A hearing protection device comprising:
   an earplug body; and
   an adjustable sound attenuation assembly,
   wherein:
   the earplug body comprises:
     a canal portion that is insertable into an ear canal of an ear;
     a canal opening at a proximal end of the canal portion that opens into the ear canal when the canal portion is inserted into the ear canal; and
     an outer portion adapted to be disposed in a concha bowl of the ear when the canal portion is inserted into the ear canal;
   the adjustable sound attenuation assembly comprises:
     an attenuator case disposed in the earplug body; and
     an attenuator insert that is removably insertable into the attenuator case;
   the attenuator case comprises:
     a hollow barrel portion that accommodates the attenuator insert therein; and
     a hollow extension portion connected to the hollow barrel portion, the hollow extension portion of the attenuator case being disposed in the canal portion of the earplug body;
   the hollow extension portion has a soundpath channel defined therethrough, the soundpath channel having a distal opening into the hollow barrel portion and a proximal opening opposite the distal opening, the soundpath channel defining a soundpath axis;
   the attenuator insert is rotatable within the hollow barrel portion of the attenuator case about an insert rotation axis, the insert rotation axis being noncollinear with the soundpath axis;
   the attenuator insert has a thickness along the soundpath axis that varies with respect to a rotation angle of the attenuator insert within the attenuator case;
   sound waves that enter the soundpath channel through the distal opening are attenuated proportionally to the thickness of the attenuator insert along the soundpath axis; and
   the thickness of the attenuator insert along the soundpath axis is defined by a distance from a flat proximal end of the attenuator insert to a sloped distal surface of the attenuator insert, the sloped distal surface having a gradual slope from a zero-attenuation groove of the attenuator insert to a maximum attenuation portion of the attenuator insert.

2. The hearing protection device of claim 1, wherein the soundpath axis is above the insert rotation axis when the canal portion of the earplug body is inserted into the ear canal, such that the soundpath axis extends into an upper portion of the ear canal and thereby minimizes intersection of the soundpath axis with deposits of cerumen in a lower portion of the ear canal.

3. The hearing protection device of claim 1, wherein the attenuator insert is formed from a surgical-grade rubber that reduces vibrations caused by incoming sound waves.

4. The hearing protection device of claim 1, wherein the attenuator case comprises a case protrusion and the attenuator insert comprises a retaining groove that engages the case protrusion and secures the attenuator insert into the attenuator case when the attenuator insert is inserted into the attenuator case.

5. The hearing protection device of claim 1, wherein the hollow barrel portion of the attenuator case is substantially cylindrical.

6. The hearing protection device of claim 1, wherein the hollow extension portion of the attenuator case is substantially cylindrical.

7. The hearing protection device of claim 1, wherein the attenuator insert further comprises a handle for rotating the attenuator insert.

8. The hearing protection device of claim 1, wherein the canal portion of the earplug body, the outer portion of the earplug body, or both, comprise cuttable portions for custom sizing of the hearing protection device for a wearer of the hearing protection device.

9. The hearing protection device of claim 1, wherein an outer surface of the earplug body is decorated with customized indicia.

10. A hearing rotection device comprising:
an earplug body; and
an adjustable sound attenuation assembly,
wherein:
the earplug body comprises:
a canal portion that is insertable into an ear canal of an ear;
a canal opening at a proximal end of the canal portion that opens into the ear canal when the canal portion is inserted into the ear canal; and
an outer portion adapted to be disposed in a concha bowl of the ear when the canal portion is inserted into the ear canal;
the adjustable sound attenuation assembly comprises:
an attenuator case disposed in the earplug body; and
an attenuator insert that is removably insertable into the attenuator case;
the attenuator case comprises:
a hollow barrel portion that accommodates the attenuator insert therein; and
a hollow extension portion connected to the hollow barrel portion, the hollow extension portion of the attenuator case being disposed in the canal portion of the earplug body;
the hollow extension portion has a soundpath channel defined therethrough, the soundpath channel having a distal opening into the hollow barrel portion and a proximal opening opposite the distal opening, the soundpath channel defining a soundpath axis;
the attenuator insert is rotatable within the hollow barrel portion of the attenuator case about an insert rotation axis, the insert rotation axis being noncollinear with the soundpath axis;
the attenuator insert has a thickness along the soundpath axis that varies with respect to a rotation angle of the attenuator insert within the attenuator case;
sound waves that enter the soundpath channel through the distal opening are attenuated proportionally to the thickness of the attenuator insert along the soundpath axis; and
the attenuator insert comprises a zero-attenuation groove defining a rotation angle of 0° when the zero-attenuation groove is disposed over the distal opening, such that when the rotation angle is 0° the thickness of the attenuator insert along the soundpath axis is zero and the sound waves that enter the soundpath channel through the distal opening are unattenuated.

11. The hearing protection device of claim 10, wherein the thickness of the attenuator insert along the soundpath axis increases gradually as the attenuator insert is rotated in a first direction from the rotation angle of 0° to a maximum attenuation rotation angle and increases abruptly as the attenuator insert is rotated in a second direction opposite the first direction from the rotation angle of 0° to the maximum attenuation rotation angle.

12. The hearing protection device of claim 11, wherein the maximum attenuation rotation angle is less than 90° relative to the rotation angle of 0° in the second direction.

13. The hearing protection device of claim 11, wherein the maximum attenuation rotation angle is less than 270° relative to the rotation angle of 0° in the first direction.

14. A hearing protection kit comprising:
an earplug body having an attenuator case therein; and
an attenuator insert that is removably insertable into the attenuator case,
wherein:
insertion of the attenuator insert into the attenuator case forms a hearing protection device comprising the earplug body, the attenuator case, and the attenuator insert;
the earplug body comprises:
a canal portion insertable into an ear canal of an ear;
a canal opening at a proximal end of the canal portion that opens into the ear canal when the canal portion is inserted into the ear canal; and
an outer portion adapted to be disposed in a concha bowl of the ear when the canal portion is inserted into the ear canal;
the attenuator case comprises:
a hollow barrel portion configured to accommodate the attenuator insert therein; and
a hollow extension portion connected to the hollow barrel portion, the hollow extension portion of the attenuator case being disposed in the canal portion of the earplug body;
the hollow extension portion has a soundpath channel defined therethrough, the soundpath channel having a distal opening into the hollow barrel portion and a proximal opening opposite the distal opening, the soundpath channel defining a soundpath axis;
the attenuator insert has an insert rotation axis, such that in the hearing protection device the attenuator insert is rotatable about the insert rotation axis within the hollow barrel portion of the attenuator case and the insert rotation axis is noncollinear with the soundpath axis;
a thickness of the attenuator insert along the soundpath axis in the hearing protection device varies with respect to a rotation angle of the attenuator insert within the attenuator case;

a maximum thickness of the attenuator insert along the soundpath axis in the hearing protection device defines a maximum attenuation of the attenuator insert;

in the hearing protection device, sound waves that enter the soundpath channel through the distal opening are attenuated proportionally to the thickness of the attenuator insert along the soundpath axis; and in the hearing protection device, the thickness of the attenuator insert along the soundpath axis is defined by a distance from a flat proximal end of the attenuator insert to a sloped distal surface of the attenuator insert, the sloped distal surface having a gradual slope from a zero-attenuation groove of the attenuator insert to a maximum attenuation portion of the attenuator insert.

15. The hearing protection kit of claim 14, further comprising at least one replacement attenuator insert configured to have the same maximum attenuation as the attenuator insert when the at least one replacement attenuator insert is used to form a hearing protection device in combination with the earplug body and the attenuator case.

16. The hearing protection kit of claim 14, further comprising at least one additional attenuator insert configured to have a different maximum attenuation from the attenuator insert when the at least one additional attenuator insert is used to form a hearing protection device in combination with the earplug body and the attenuator case.

17. The hearing protection kit of claim 14, wherein an outer surface of the earplug body is decorated with customized indicia.

\* \* \* \* \*

UNITED STATES PATENT AND TRADEMARK OFFICE
CERTIFICATE OF CORRECTION

PATENT NO. : 8,931,489 B2  
APPLICATION NO. : 13/735177  
DATED : January 13, 2015  
INVENTOR(S) : Jeremiah Smith It is certified that error appears in the above-identified patent and that said Letters Patent is hereby corrected as shown below:

In the specification

Col. 2, Line 12,
"tion kits may rotatable within the hollow barrel portion of the" should read
--tion kits may be rotatable within the hollow barrel portion of the--;

Col. 6, Line 47,
"to be sufficiently large such that it the quality, integrity, and/or" should read
--to be sufficiently large such that the quality, integrity, and/or--;

Col. 7, Line 5,
"it the quality, integrity, and/or charity of sound entering the" should read
--the quality, integrity, and/or charity of sound entering the--;

Col. 7, Line 29,
"minimizes intersection of the soundpath axis 50 with such" should read
--minimize intersection of the soundpath axis 50 with such--;

Col. 10, Line 38,
"or may alternate from thick to thin multiple time within one" should read
--or may alternate from thick to thin multiple times within one--; and Col. 11, Line 2,
"may rotatable within the hollow barrel portion 210 of the" should read
--may be rotatable within the hollow barrel portion 210 of the--.

Signed and Sealed this
Twenty-third Day of February, 2016

Michelle K. Lee
*Director of the United States Patent and Trademark Office*